(12) United States Patent
Beuschel et al.

(10) Patent No.: US 6,769,912 B2
(45) Date of Patent: Aug. 3, 2004

(54) DEVICE FOR PRODUCING A DENTAL REPLACEMENT PART

(75) Inventors: Martin Beuschel, München (DE); Erich Huber, Tyrlaching (DE); Erich Sendelbach, Peissenberg (DE); Olaf Schäfer, Singen (DE)

(73) Assignee: 3M ESPE AG (DE)

( * ) Notice: Subject to any disclaimer, the term of this patent is extended or adjusted under 35 U.S.C. 154(b) by 222 days.

(21) Appl. No.: 10/167,594

(22) Filed: Jun. 13, 2002

(65) Prior Publication Data

US 2002/0182566 A1 Dec. 5, 2002

Related U.S. Application Data

(62) Division of application No. 09/385,368, filed on Aug. 30, 1999, now Pat. No. 6,454,568.

(30) Foreign Application Priority Data

Aug. 28, 1998 (DE) ...................................... 298 15 486 U

(51) Int. Cl.[7] .................................................. A61C 3/00
(52) U.S. Cl. ........................... 433/163; 433/223; 264/19
(58) Field of Search ................................ 433/223, 163, 433/215, 25; 206/63.5, 368; 264/19, 20; 249/54; 269/17, 287, 909

(56) References Cited

U.S. PATENT DOCUMENTS

| | | | |
|---|---|---|---|
| 1,796,470 A | 3/1931 | Meyer | |
| 1,899,718 A | 2/1933 | Poston | |
| 2,355,853 A | * 8/1944 | James | ......................... 164/65 |
| 2,409,783 A | 10/1946 | Moskey | |
| 3,276,122 A | * 10/1966 | Slayton | ...................... 433/72 |
| 5,383,752 A | 1/1995 | Rheinberger et al. | |
| 5,490,810 A | 2/1996 | Hahn et al. | |
| 6,224,371 B1 | * 5/2001 | De Luca | ..................... 433/49 |

FOREIGN PATENT DOCUMENTS

| | | |
|---|---|---|
| EP | A 455 854 A1 | 11/1991 |
| EP | 0 807 422 | 11/1997 |
| WO | WO 95/30382 | 11/1995 |

* cited by examiner

*Primary Examiner*—Todd E. Manahan
(74) *Attorney, Agent, or Firm*—Connolly Bove Lodge & Hutz LLP

(57) ABSTRACT

In a device for the automatic production of dental replacement parts, a blank 13 is fitted in a substantially plate-shaped carrier body 10 which is so dimensioned that the blank 13 does not exceed the carrier body 10 in any direction. The carrier body 10 serves not only for holding the blank 13 in the working machine but also for protecting it during its automatic handling in magazines or the like. The carrier body 10 is provided with a bar code 20 which relates to the material and dimensions of the blank 13 and may identify data according to which the blank 13 is to be worked The bar code 20 is adapted to be changed by the working machine so as to prevent the carrier body 10 from being reused with the same or a different blank 13.

6 Claims, 1 Drawing Sheet

U.S. Patent		Aug. 3, 2004		US 6,769,912 B2
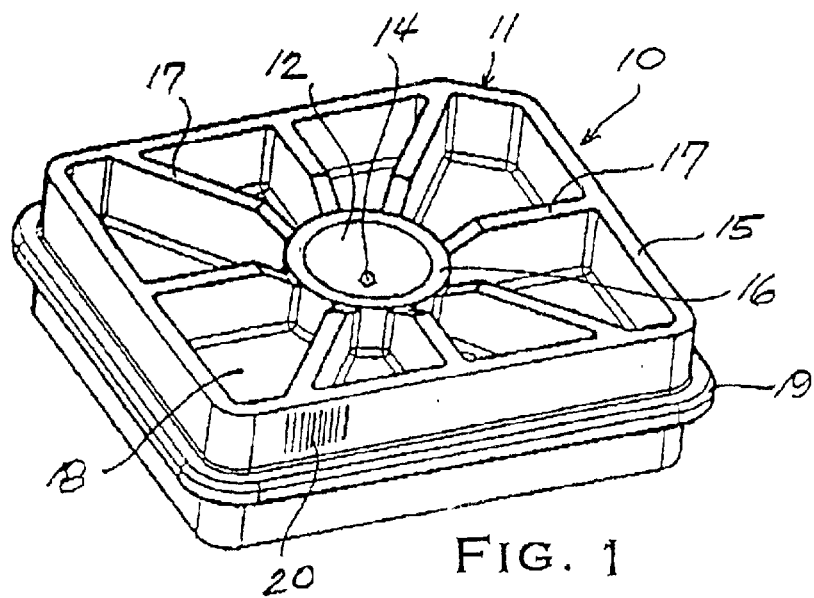
FIG. 1
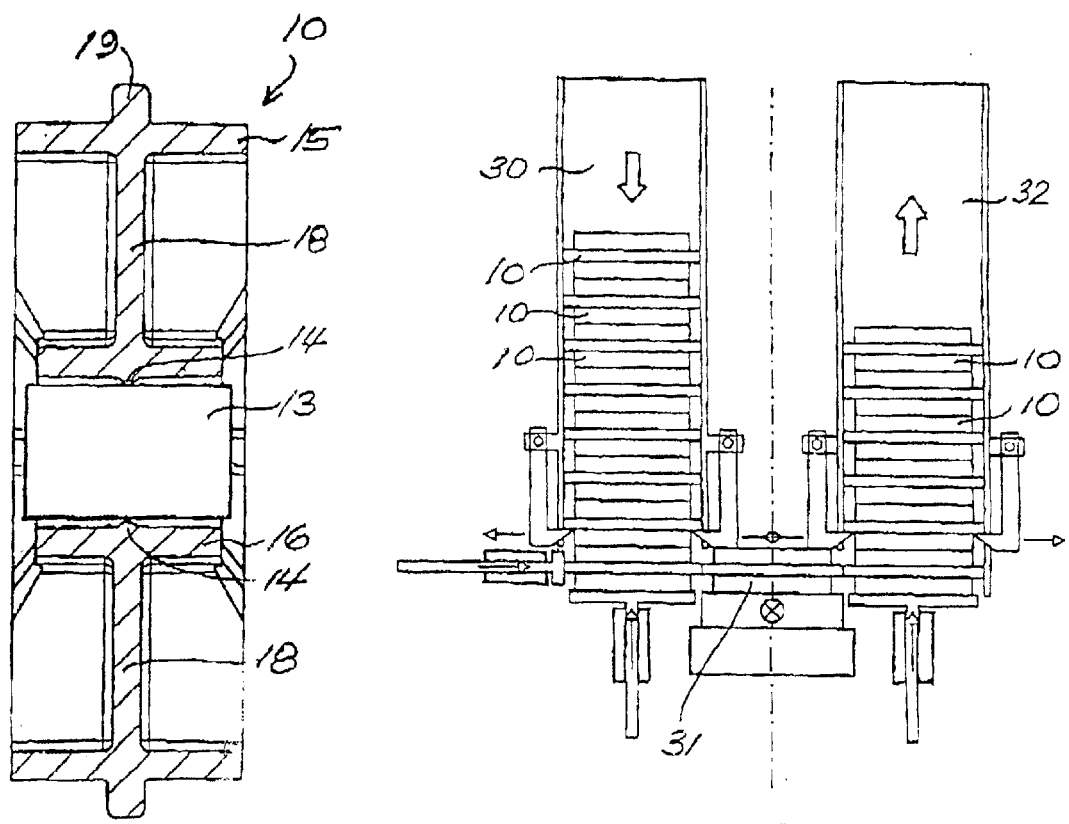
FIG. 2
FIG. 3

DEVICE FOR PRODUCING A DENTAL REPLACEMENT PART

This application is a divisional of U.S. Ser. No. 09/385,368, filed Aug. 30, 1999 now U.S. Pat. No. 6,454,568.

BACKGROUND OF THE INVENTION

Dental replacement parts, such as crowns, bridges, implants or the like, can be produced by first scanning the prepared tooth stump as a gypsum model using an optical or mechanical scanner, and then creating milling curves for the cavity of the tooth replacement part using the data obtained by the scanning. A wax prosthesis formed by the dental technician is then placed on the gypsum model of the stump and is scanned for obtaining additional data for generating the milling curve. Both sets of data represent in a coordinate system the volume to be milled. Alternatively, the tooth replacement placement part may already be present in digital form in standard libraries and adapted to the respective individual situation.

PCT publication No. WO 95/30382 discloses a device for holding blanks used in the production of dental replacement parts by a milling or other machining tool. For economical reasons, the tooth replacement blank is so dimensioned that the working results in minimum waste the expensive blank material. The generally cylindrical blank is glued into a cylindrical carrier body which surrounds the blank in a partial area of its axial length and is adapted to be inserted in the respective machine tool.

In the system disclosed in European patent publication No. 0 455 854, a tooth replacement blank is worked from a slab of material in such a way that both a tooth crown and a holding stump are created. Upon severing the crown, a bore of the crown is fitted on a conical end of the holding stump.

SUMMARY OF THE INVENTION

It is an object of the invention to provide a receptacle for a tooth replacement blank which serves not only for holding the blank in the respective machine tool but at the same time represents a primary package for protecting the blank and handling it safely in the course of an automatic production process.

This object is met in accordance with the invention by a device for producing a dental replacement part, including a blank and a carrier body, the carrier body having an inner side holding the blank and an outer side adapted to be fitted in a working tool, wherein the carrier body is dimensioned so that the blank does not extend beyond the carrier body in any direction.

The fact that the blank does not extend beyond the carrier body in any direction results in an effective protection of the blank material against mechanical influences. Moreover, the blank may be worked from two opposite sides, which is essential for tooth replacements. Since it is solely the carrier body which defines the outer shape of the unit formed by the blank and the carrier body, the carrier body may be designed without limitations in such a way that it may be stacked with other units irrespective of the exact shape of the blank and automatically fed, withdrawn and turned in the course of an automatic production.

In a preferred embodiment, the carrier body is substantially plate-shaped and has an opening for receiving the blank, the through length of the opening being not smaller than the axial dimension of the blank. The plate shape of the carrier body is particularly advantageous for handling and stacking.

The carrier body is preferably formed with a recess from at least one of its end surfaces to form a peripheral flange and a receiving cylinder surrounding the opening. The recess form ribs which extend radially between the peripheral flange and the receiving cylinder. This results in a high rigidity at low material consumption.

In accordance with another preferred embodiment, the peripheral flange defines the largest height of the carrier body and the receiving cylinder is recessed in both axial directions with respect to the peripheral flange. The overall dimensions of the carrier body are thus determined by its outer part, whereas its inner part surrounding the blank is smaller thereby rendering the blank readily accessible for the working tool.

Since the carrier body according to the invention may be designed substantially independently of the size and shape of the blank, it provides sufficient space for receiving a code related to the blank preferably to the dimensions and/or material thereof. The machine tool may be designed such that, by means of the code scanned from the carrier body, it automatically performs the proper process step with the proper tool for the blank contained in the carrier body, or suppresses the working step in case of non-coincidence.

Advantageously, the code is adapted to be changed by the working tool This prevents an inadvertent double working of the same blank. At the same time, this feature guarantees that only original blanks, as provided by the producer including the carrier body, are worked whereas used carrier bodies re-fitted with blanks, are rejected.

In yet another embodiment of the invention, the carrier body has a non-symmetrical outer shape to permit the carrier body including the blank to be properly oriented within the machine tool.

With a view to material expense and manufacturing costs, the carrier body is preferably formed of synthetic material by injection moulding.

BRIEF DESCRIPTION OF THE DRAWING

FIG. 1 is a perspective view of the carrier body for a dental replacement blank, FIG. 2 is an axial cross-section through the carrier body of FIG. 1, with a blank inserted, and FIG. 3 is a schematic representation of the magazine of an automatic working machine.

DETAILED DESCRIPTION OF PREFERRED EMBODIMENT

Referring to FIGS. 1 and 2, the carrier body 10, which is produced by injection moulding of synthetic material, is substantially plate-shaped with a rectangular basis and a height that is smaller than the sides of the basis. A corner portion 11 is chamfered to allow the orientation of the carrier body 10 to be determined.

A substantially central bore 12 serves to receive a dental replacement blank 13 (FIG. 2). The substantially cylindrical blank 13 is held in position by three noses 14 which are provided on the inner wall of the bore 12 and are mutually offset by 120°. The blank 13 may be glued, screwed or otherwise mounted within the bore 12.

Instead of the single bore 12 shown in the drawing, a plurality of bores may be provided for receiving a plurality of blanks in one carrier body 10. Further, an angular or otherwise designed receiving opening may be provided depending on the shape of the blank 13.

The carrier body 10 has recesses extending from both end faces, the recesses being dimensioned and arranged so as to leave a peripheral flange 15, a receiving cylinder 16 defining the bore 12, eight ribs 17 extending radially between the peripheral flange 15 and the receiving cylinder 16, and an intermediate wall 18 situated approximately midway between the two end surfaces. A continuous bead 19 is provided on the peripheral flange 15 approximately at the centre of the height thereof.

As is seen particularly in FIG. 2, the greatest thickness of the plate-shaped carrier body 10 is determined by the height of the peripheral flange 15 measured in the axial direction of the bore 12. This height is greater than the axial length of the blank 13. The carrier body 10 thus extends beyond the blank 13 in all directions, thereby protecting the blank 13 against mechanical damages.

The axial length of the receiving cylinder 16 is smaller than the height of the peripheral flange 15 and also smaller than the axial length of the blank 13 so that the latter, though being recessed within the outer dimensions of the carrier body 10, projects beyond the parts immediately receiving the blank 13, and is therefore well accessible for being worked.

The peripheral flange 15 carries a bar code 20 at at least one position which may be imprinted directly on the flange 15 or on a strip pasted thereto, or may be moulded in the material of the carrier body 10. The bar code 20 serves to identify the material, dimensions and/or other properties of the blank 13 contained in the carrier body 10.

Instead of the bar code 20, any other type of machine-readable code may be provided. Alternatively, the code may be transmitted from a transponder attached to the carrier body 10.

FIG. 3 illustrates a way of using the carrier body 10 including the blank 13 of FIGS. 1 and 2 in the course of an automatic working process. A plurality of carrier bodies 10 with raw blanks are inserted in a feeding magazine 30. The magazine 30 is provided with an oblique surface (not shown) which cooperates with the chamfered corner portions 11 of the carrier bodies 10 to ensure that the carrier bodies are inserted in proper orientation. At the lower end of the magazine 30 shown in FIG. 3, the respective front carrier body 10 is transferred to the working position shown at 31. Upon working, the carrier body 10 including the worked blank 10 is transferred to a withdrawal magazine 32 shown at the right in FIG. 3.

In the course of the working process, the bar code 20 provided on the carrier body 10 is changed by the working tool. The change may reside in a deletion of part or all of the code. This prevents the same blank from being worked twice and prevents used carrier bodies from being re-fitted with foreign blanks and re-used in a working process.

Instead of changing the code, the control of the working machine may be provided with a memory which stores an identification number contained in the bar code 20 and compares the code of any newly supplied carrier body 10 with the contents of the memory.

The same bar code 20 or an additional code (not shown) may be further used to identify the individual working program to be performed on the respective blank 13. This program may contain the individual working data which were obtained by the optical or mechanical scanning explained above. In such a case, the various carrier bodies 10 with their blanks 13 may be inserted in the feeding magazine 30 in any desired sequence, and by referring to the code the working machine can select the proper program or, in case the program has not yet been loaded, postpone the working of the respective blank.

What is claimed is:

1. A device for producing a dental replacement part, comprising:
    a carrier body having a pair of opposite sides;
    a recess formed in the carrier body and extending between said opposite sides;
    a blank having a length less than the distance between the opposite sides of the carrier body, the blank being received in the recess and having transverse ends recessed inwardly relative to the opposite sides of the carrier body; and
    means for holding the blank within the recess.

2. The device of claim 1, further comprising a peripheral edge located between the opposite sides of the carrier body, the edge having a peripheral flange extending therefrom.

3. The device of claim 2, wherein the recess is located in the center of the body and further wherein the opposite sides of the carrier have ribs formed therein that extend radially between the peripheral flange and the recess.

4. The device of claim 1, wherein the carrier body further comprises means thereon that are associated with data relating to the blank.

5. The device of claim 1, wherein the carrier body has a non-symmetrical peripheral shape.

6. A device for producing dental replacement parts, comprising:
    a carrier body having upper and lower sides;
    a cylinder located in a central part of the body and having transverse ends respectively recessed relative to the upper and lower sides;
    a bore formed axially through the recessed cylinder;
    a blank having a length less than that of the bore;
    the blank being entirely received in the bore and having transverse ends recessed inwardly relative to respective transverse ends of the cylinder; and
    means for holding the blank within the bore.

* * * * *

UNITED STATES PATENT AND TRADEMARK OFFICE
CERTIFICATE OF CORRECTION

PATENT NO. : 6,769,912 B2
DATED : August 3, 2004
INVENTOR(S) : Beuschel, Martin

It is certified that error appears in the above-identified patent and that said Letters Patent is hereby corrected as shown below:

Title page,
Item [57], ABSTRACT,
Line 10, after "worked" insert -- . --.

Column 1,
Line 18, after "replacement" delete "placement".

Column 2,
Line 25, after "tool" insert -- . --.

Column 3,
Line 22, delete "at" before "least".
Line 38, delete "comer" and insert -- corner --, therefore.

Signed and Sealed this

Twelfth Day of July, 2005

JON W. DUDAS
*Director of the United States Patent and Trademark Office*